United States Patent
Horn

(10) Patent No.: US 10,327,632 B2
(45) Date of Patent: Jun. 25, 2019

(54) SYSTEMS AND METHODS FOR WIDE FIELD-OF-VIEW OPTICAL COHERENCE TOMOGRAPHY

(71) Applicant: NOVARTIS AG, Basel (CH)

(72) Inventor: Jochen Horn, Irvine, CA (US)

(73) Assignee: NOVARTIS AG, Basel (CH)

(*) Notice: Subject to any disclaimer, the term of this patent is extended or adjusted under 35 U.S.C. 154(b) by 24 days.

(21) Appl. No.: 15/844,914

(22) Filed: Dec. 18, 2017

(65) Prior Publication Data

US 2018/0168445 A1 Jun. 21, 2018

Related U.S. Application Data

(60) Provisional application No. 62/436,732, filed on Dec. 20, 2016.

(51) Int. Cl.
*A61B 3/10* (2006.01)
*G01B 9/02* (2006.01)
(Continued)

(52) U.S. Cl.
CPC .......... *A61B 3/102* (2013.01); *G01B 9/02032* (2013.01); *G06T 1/0007* (2013.01);
(Continued)

(58) Field of Classification Search
CPC .. A61B 3/102; G01B 9/02032; G06T 3/0018; G06T 1/0007; G06T 5/00; G06T 2207/10101
See application file for complete search history.

(56) References Cited

U.S. PATENT DOCUMENTS 7,884,945 B2   2/2011 Srinivasan et al.
8,777,412 B2   7/2014 Buckland et al.
(Continued)

FOREIGN PATENT DOCUMENTS

EP    2859838 A1   4/2015
WO    2016/111248 A1   7/2016
WO    2016/178298 A1   11/2016

OTHER PUBLICATIONS

Ali M and Parlapalli R, "Signal Processing Overview of Optical Coherence Tomography Systems for Medical Imaging", Biomedical Optics Express, May 2015, vol. 6, No. 5, pp. 1534-1552.
(Continued)

*Primary Examiner* — Jack Dinh

(57) ABSTRACT

An optical coherence tomography (OCT) system includes a light source configured to generate an OCT beam and a beam splitter, configured to split the OCT beam into a reference beam and an imaging beam, direct the reference beam toward a reflector, and direct the imaging beam toward a scanner. The system includes a linear actuator, such as a piezoelectric or voice coil, configured to move the reflector to adjust the length of the reference beam and the scanner, configured to scan the imaging beam onto a target surface at a plurality of scan angles, wherein the scanner and target surface are separated by a sample distance that varies at each of the scan angles. The system further includes an OCT controller comprising a processor and instructions stored on a memory, the instructions executable by the processor to cause the OCT controller to generate signals to cause the scanner to scan the imaging beam at each of the scan angles at a first scan rate, and cause the actuator to adjust the length of the reference beam during the scan synchronously with the scan rate to offset the variation in sample distance at each of the scan angles.

19 Claims, 4 Drawing Sheets

(51) Int. Cl.
*G06T 1/00* (2006.01)
*G06T 3/00* (2006.01)
*G06T 5/00* (2006.01)

(52) U.S. Cl.
CPC .............. *G06T 3/0018* (2013.01); *G06T 5/00* (2013.01); *G06T 2207/10101* (2013.01)

(56) References Cited

U.S. PATENT DOCUMENTS

| | | |
|---|---|---|
| 9,339,178 B2 | 5/2016 | Yu et al. |
| 2010/0302508 A1 | 12/2010 | Yamamoto et al. |
| 2012/0189184 A1 | 7/2012 | Matsumoto et al. |

OTHER PUBLICATIONS

Fujimoto et al., "Biomedical Optical Imaging", Chapter 26, Progress Report of the Research Laboratory of Electronics (RLE) at MIT, No. 152, (2009-2010), pp. 26-1 thru 26-57.

Kolb et al, "Ultra-widefield retinal MHz-OCT imaging with up to 100 degrees viewing angle", Biomedicl Optics Express, May 2015, vol. 6, No. 5, pp. 1534-1552.

SYSTEMS AND METHODS FOR WIDE FIELD-OF-VIEW OPTICAL COHERENCE TOMOGRAPHY

FIELD

The present disclosure relates to medical device imaging systems, including optical coherence tomography (OCT) systems.

BACKGROUND

Optical Coherence Tomography (OCT) is an imaging technique widely adopted in the biomedical fields, including ophthalmology. OCT systems perform high-resolution, cross sectional imaging in semitransparent samples (such as biological tissues) by measuring the echo time delay of reflected light. OCT is often used by ophthalmic surgeons to assist with precision cutting and/or removal of tissues such as the vitreous. Providing wide-field-of-view OCT imaging across a curved surface such as a retina can be challenging because the images become curved and distorted at wide scan angles, particularly in highly myopic patients. Accordingly, there exists a need for improved wide-field-of-view OCT imaging in the ophthalmic context.

SUMMARY

In certain embodiments, an optical coherence tomography (OCT) system includes a light source configured to generate an OCT beam and a beam splitter, configured to split the OCT beam into a reference beam and an imaging beam, direct the reference beam toward a reference reflector, and direct the imaging beam toward a scanner. The system also includes a linear actuator, such as a piezoelectric actuator or voice coil actuator, configured to move the reference reflector to adjust the length of the reference beam and the scanner, configured to scan the imaging beam onto a target surface at a plurality of scan angles, wherein the scanner and target surface are separated by a sample distance that varies at each of the scan angles. The system further includes an OCT controller comprising a processor and instructions stored on a memory, the instructions executable by the processor to cause the OCT controller to generate signals to cause the scanner to scan the imaging beam at each of the scan angles at a first scan rate, and cause the actuator to adjust the length of the reference beam during the scan synchronously with the scan rate to match the variation in sample distance at each of the scan angles.

In certain embodiments, the scan rate is between 200 Hz and 400 Hz, or is at least 300 Hz. The scanner may be configured to scan the imaging beam at each of the scan angles according to a raster pattern, and the raster pattern may generate a B-scan at least 12 mm in length or at least 16 mm in length.

In certain embodiments, the linear actuator is configured to translate the reference reflector at least 2 mm in a direction parallel to the reference beam. The linear actuator may further be configured to translate the reference reflector at least 4 mm in a direction parallel to the reference beam.

The OCT system may comprise a spectral-domain OCT (SD-OCT) system or a swept-source OCT (SS-OCT) system.

In certain embodiments, an optical coherence tomography (OCT) system, comprises a light source configured to generate an OCT beam, and a beam splitter, configured to split the OCT beam into a reference beam and an imaging beam, direct the reference beam toward a reference reflector, and direct the imaging beam toward a scanner. The system also includes a linear actuator, such as a piezoelectric actuator or voice coil actuator, configured to move the reference reflector to change the length of the reference beam, and the scanner, configured to scan the imaging beam onto a target surface over a plurality of scan angles, wherein the scanner and target surface are separated by a first sample distance at a first scan angle and a second sample distance at a second scan angle. The system includes an OCT controller comprising a processor and instructions stored on a memory, the instructions executable by the processor to cause the OCT controller to generate signals to cause the scanner to scan the imaging beam onto the target surface at the first scan angle and the second scan angle according to a scan rate, and cause the actuator to move the reference reflector synchronously with the scan rate while the scanner scans the imaging beam onto the target surface, thereby adjusting the length of the reference beam to account for a difference between the first sample distance and the second sample distance. The system further includes a detector configured to receive the reference beam reflected by the reference reflector and the imaging beam reflected by the target surface, and output an interference signal based on the received reference beam and the imaging beam.

In certain embodiments, the linear actuator comprises a piezoelectric stack or voice coil configured to translate the reference reflector at least 2 mm in a direction parallel to the reference beam. In certain embodiments, the first scan angle and the second scan angle are separated by at least 20 degrees. In certain embodiments, the scan generates a B-scan at least 12 mm in length. The OCT system may comprise a spectral-domain OCT (SD-OCT) system or a swept-source OCT (SS-OCT) system.

According to certain embodiments, an optical coherence tomography (OCT) system comprises a light source, configured to generate an OCT beam, and a beam splitter, configured to split the OCT beam into a reference beam and an imaging beam, direct the reference beam toward a reference reflector, and direct the imaging beam toward a scanner. The system further includes a linear actuator, configured to translate the reference reflector at least 2 mm in a direction parallel to the reference beam and the scanner, configured to scan the imaging beam onto a target surface at a plurality of scan angles. The system includes an OCT controller comprising a processor and instructions stored on a memory, the instructions executable by the processor to cause the OCT controller to generate signals to cause the scanner to scan the imaging beam at each of the scan angles at a first scan rate, and cause the actuator to translate the reference reflector synchronously with the scan rate, such that a path length of the reference beam is maintained within a tolerance range of a path length of the imaging beam throughout the scan.

In certain embodiments, the tolerance range is less than 0.5 mm or 1 mm. The scan rate may be between 200 Hz and 400 Hz. Further, the scanner may be configured to scan the imaging beam at each of the scan angles according to a raster pattern. The linear actuator may be a piezoelectric stack or voice coil configured to translate the reference reflector at least 2 mm in a direction parallel to the reference beam.

Certain embodiments may provide one or more technical advantages. For example, improved OCT imaging systems according to the disclosure may provide ultra-wide field-of-view OCT imaging with reduced distortion. Certain embodiments generate OCT images in which a target surface is centered throughout an OCT image window, despite relative variations in target depth. Thus, certain embodiments provide improved live OCT imaging of curved surfaces, such as high-myopia retinal surfaces. These and other advantages will be apparent to those skilled in the art in view of the present drawings and specification.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
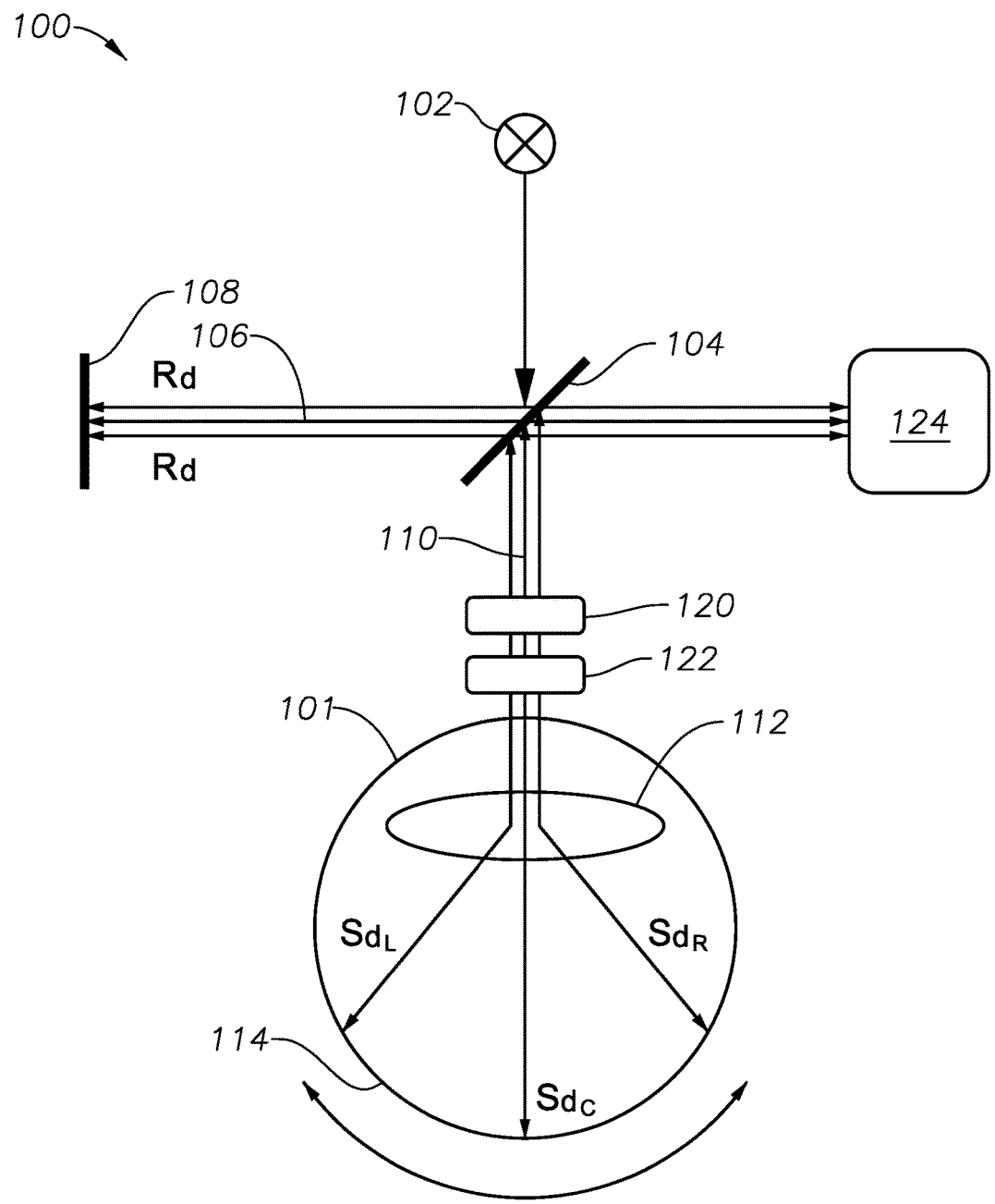
FIG. 1 illustrates a block diagram of a conventional OCT system.

One skilled in the art will understand that the drawings, described below, are for illustration purposes only, and are not intended to limit the scope of applicant's disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Alterations and further modifications to the described systems, devices, and methods, and any further application of the principles of the present disclosure are contemplated as would normally occur to one skilled in the art to which the disclosure relates. In particular, it is contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

Optical coherence tomographic (OCT) imaging systems are useful in an array of biological applications including ophthalmology, dentistry, cardiology, gastroenterology, and others. The general design and principles of OCT systems are known and described in, for example: (a) "Signal Processing Overview of Optical Coherence Tomography Systems for Medical Imaging," Texas Instruments White Paper SPRABB9 (June 2010) and (b) "Biomedical Optical Imaging," Progress Report of the Research Laboratory of Electronics at MIT, No. 152 (2009-2010), each of which is incorporated by reference herein in its entirety.

FIG. 1 is a simple schematic illustration of components in a conventional OCT system 100. System 100 may comprise a spectral-domain OCT (SD-OCT) system or swept-source (SS-OCT) system. In general, the components of such systems 100 are well-known to the skilled artisan. Among other things, system 100 includes a light source 102, beam splitter/combiner 104, reference reflector 108, scanner 120, and a detector 124. Light source 102 may comprise any suitable low-coherence light source such as a super-luminescent diode, ultrashort (e.g., femtosecond) pulsed laser, or supercontinuum laser, and may comprise a frequency-swept or tunable laser in certain examples, such as SS-OCT systems. Beam splitter 104 may comprise a non-polarized beam splitter for splitting the OCT beam into an imaging beam and a reference beam and combining or directing reflected imaging and reference light toward detector 124. Reference reflector 108 is typically a mirror, but may comprise any suitable component which reflects the reference beam 106 toward the detector 124. Scanner 120 may comprise one or more galvanometer-controlled mirrors to scan the imaging beam in the x-y plane toward a target or sample, such as retina 114 (when discussing the object being imaged, the terms "target" and "sample" are used interchangeably herein). In certain embodiments, scanner 120 may additionally include focusing optics to scan the imaging beam in a z-direction. Scanner 120 may comprise any suitable scanning mirror arrangement. Alternatively, scanner 120 may comprise any suitable scanner components, such as microelectromechanical systems (MEMS) or a resonant scanner. The imaging beam scanned by scanner 120 is directed through optical elements 122 which may comprise focusing and/or collimating lenses. Detector 124 comprises an interferometer which receives the imaging beam reflected from the target and the reference beam reflected from the reflector 108 and outputs an interference signal from which an OCT image can be generated. Particular components included in detector 124 depend on the type of OCT system and may include any suitable combination of spectrometers, photodetectors, array detectors, analog-to-digital converters (ADCs), diffraction grating(s), or other components known to those skilled in the art. For example, detector 124 in an SD-OCT system may include a diffraction grating, lenses, and an array detector such as a charge-coupled device (CCD). As another example, detector 124 in an SS-OCT system may include a photodetector and a analog-to-digital converter.

System 100 may include an OCT controller (not shown in FIG. 1) comprising hardware, firmware, and software configured to control components of system 100 to acquire and display OCT images of a target. System 100 may additionally include one or more displays (not shown) to present OCT images generated by the OCT controller. In various examples, the display may include any one or more monitors, projectors, oculars, heads-up displays, screens, glasses, goggles, etc. The OCT images may be displayed as 2D or 3D images.

In operation, light source 102 emits a low-coherence light beam directed to beam splitter 104, which splits the light into a reference beam 106 directed through a reference arm (which may comprise any suitable transmission and focusing optics including optical fibers) toward reflector 108 and an imaging beam 110 directed through an imaging arm (which likewise may include any suitable transmission and focusing optics including optical fibers) toward a scanner 120. Scanner 120 (under the control of the OCT controller) may scan the imaging beam toward optics 122 and the lens 112 of eye 101 according to a scan pattern (e.g., raster scan, radial scan, cube scan, circle group scan, line group scan, etc.) to generate the desired scan (e.g., A-scan, B-scan, or C-scan). A depth-resolved axial scan (A-scan) comprises a measurement of the light signal interference at a point. Cross-sectional images (B-scans) may be generated by scanning the OCT beam across the tissue surface and acquiring multiple axial measurements over a line, curve, circle, etc. A 3D image may be constructed from a series of B-scans generated over an area of the tissue surface. Scanning may be repeated at a scan rate or frequency to generate live or real-time OCT images which may useful for pre-operative diagnostics as well as intra-operative guidance.

Imaging beam light reflected by the retina 114 and reference beam light reflected by the reflector 108 may be received at detector 124, which interferes the back-reflected or backscattered imaging beam with the reference beam to generate OCT images. Interference occurs when the path length of the reference beam (i.e., the distance imaging light travels between source 102 and reflector 108) and the path length of the imaging beam (i.e., the stance imaging light travels between source 102 and a target such as retina 114) are matched within the coherence length of the light emitted by light source 102. This interference signal conveys information about the target at a depth which corresponds to the reference beam path length.

Accordingly, OCT systems are calibrated prior to use by setting the reference beam path length according to the target depth, so that the path length of the reference beam is approximately equal to the path length of the imaging beam at the target depth. The difference between the path length of the reference beam and the path length of the imaging beam at the target depth in an OCT system is referred to as the optical path difference (OPD). Ideally, OPD is zero, though absolute precision necessary in practice. Thus, in the example of FIG. 1, if the primary target depth is the center surface of retina 114, the reference beam path length (illustrated as reference beam distance Rd) is set to match the path length of the imaging beam measured to the center of retina 114 (illustrated as center sample distance $Sd_C$). In conventional spectral-domain OCT (SD-OCT) systems or swept-source OCT (SS-OCT) systems such as system 100, this reference beam path length is fixed at the outset of the imaging procedure and remains fixed throughout the OCT scan.

It is noted that OCT imaging systems may be broadly classified into time-domain OCT (TD-OCT) systems, SD-OCT systems, and SS-OCT systems. TD-OCT systems obtain an interference pattern by moving a reference mirror to vary the reference path length at each point in a scan pattern. That is, at a given point in a TD-OCT scan pattern, the reference mirror in the reference arm must be moved to change the reference path length. The movement of this mirror in the reference arm of TD-OCT systems is a speed gating factor, because the mirror must be moved through a distance (z-range) at each (x,y) point of an OCT scan pattern in order to generate the required interference signal.

Conventional SD-OCT and SS-OCT systems operate according to different principles and avoid this speed gate by employing a fixed-position reference reflector which requires no mechanical scanning of the reference path at any point in a scan pattern. SD-OCT systems use a broadband light source and obtain depth information measuring the spectral density in the sample arm using a spectrometer. SS-OCT systems utilize a frequency-swept laser or tunable laser and a single-point detector. In both SD-OCT and SS-OCT systems, OCT images are generated from the received interference signal using fast Fourier transforms. Accordingly, the reference reflector position is fixed at each (x,y) point of an OCT scan pattern executed by conventional SD-OCT and SS-OCT systems.

Typical SD-OCT and SS-OCT systems for posterior-segment imaging may scan between 20° and 40° (e.g., ±10° or ±20° from a center position) across a retinal target. Over such scan angles, the targeted portion of the retina may be imaged without significant distortion because variations in the depth of the retina attributable to retinal curvature are not significant. Stated differently, the variations in OPD resulting from retinal curvature are typically not very significant across smaller scan angle ranges (e.g., between 20° and 40°). However, over wider fields-of-view (e.g., 40° or more), the curvature of the retina across the imaged area results in significant variation in OPD, particularly in high-myopia patients. This variation in OPD can cause distortion in the OCT image.

Figure 2:
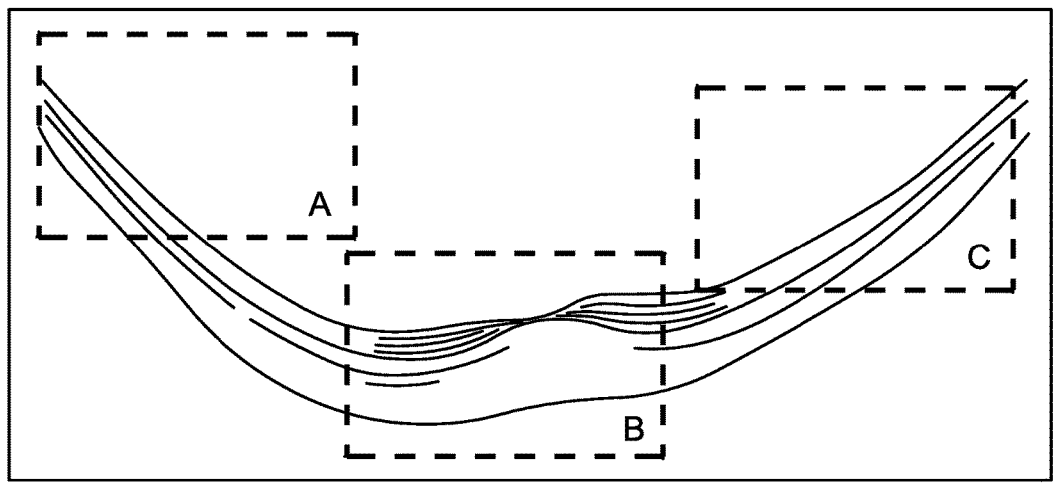
FIG. 2 illustrates a retinal image generated by a conventional OCT imaging system.

FIG. 2 illustrates an example wide field-of-view B-scan (approximately) 40° of a retina generated by a conventional SD-OCT or SS-OCT system. As illustrated in this example, the image of the retina is curved in a wide "U" shape, such that the edges appear to "fall off" the image range on each side. This distortion results from variations in the OPD attributable to retinal curvature and the fixed reference beam path length. That is, the reference beam path length is calibrated to image at a particular depth, e.g., so that the OPD is approximately zero at the center of the retina. However, the natural curvature of the retina results in the fundus surface outside that depth because the OPD changes as the imaging beam is scanned across tissues which are closer to scanner 120.

This characteristic "U"-shaped distortion is undesirable and problematic. For example, during a procedure, a surgeon may "zoom in" to a particular area of the retina, such one of windows A-C. Each of windows A-C represents an image area for enlargement, though it is noted that any portion of the image may be enlarged. Although the retinal image is generally horizontal in window B, windows A and C each display a portion of the retinal surface with a steep angular orientation in the image window. This angular orientation results in distortion and truncation of the retinal image and, among other things, it makes the image more difficult to read and use, particularly in an intra-operative context.

Figure 3:
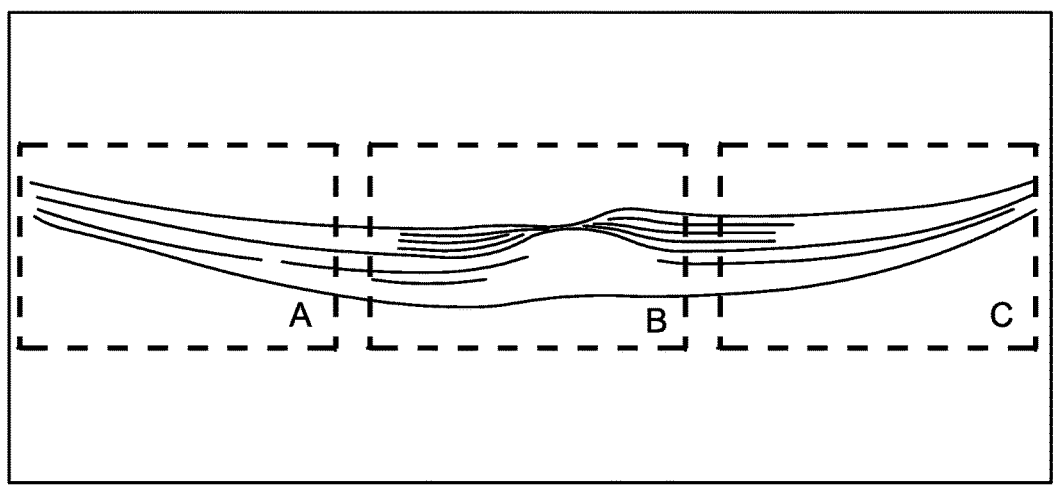
FIG. 3 illustrates a retinal image generated by an improved OCT imaging system according to certain embodiments.

Embodiments of the present disclosure address this problem by modulating the position of a reference reflector, thereby adjusting the reference beam path length to account for or match variations of the target depth within a scan and "flatten" out the OCT image as shown in FIG. 3. In other words, the position of the reference reflector is modulated so that the system OPD is maintained at or near zero throughout a scan pattern. Compared against FIG. 2, image windows A and C of FIG. 3 display larger portions of the retina with increased clarity and reduced distortion. Accordingly, improved OCT systems according to the present disclosure facilitate high-speed (e.g., 200-400+Hz), wide-angle scans (e.g., ±20°-±90° sweeps) across large retinal cross-sections and provide improved images that are substantially free of distortion and easy to use during a surgical procedure.

Figure 4:
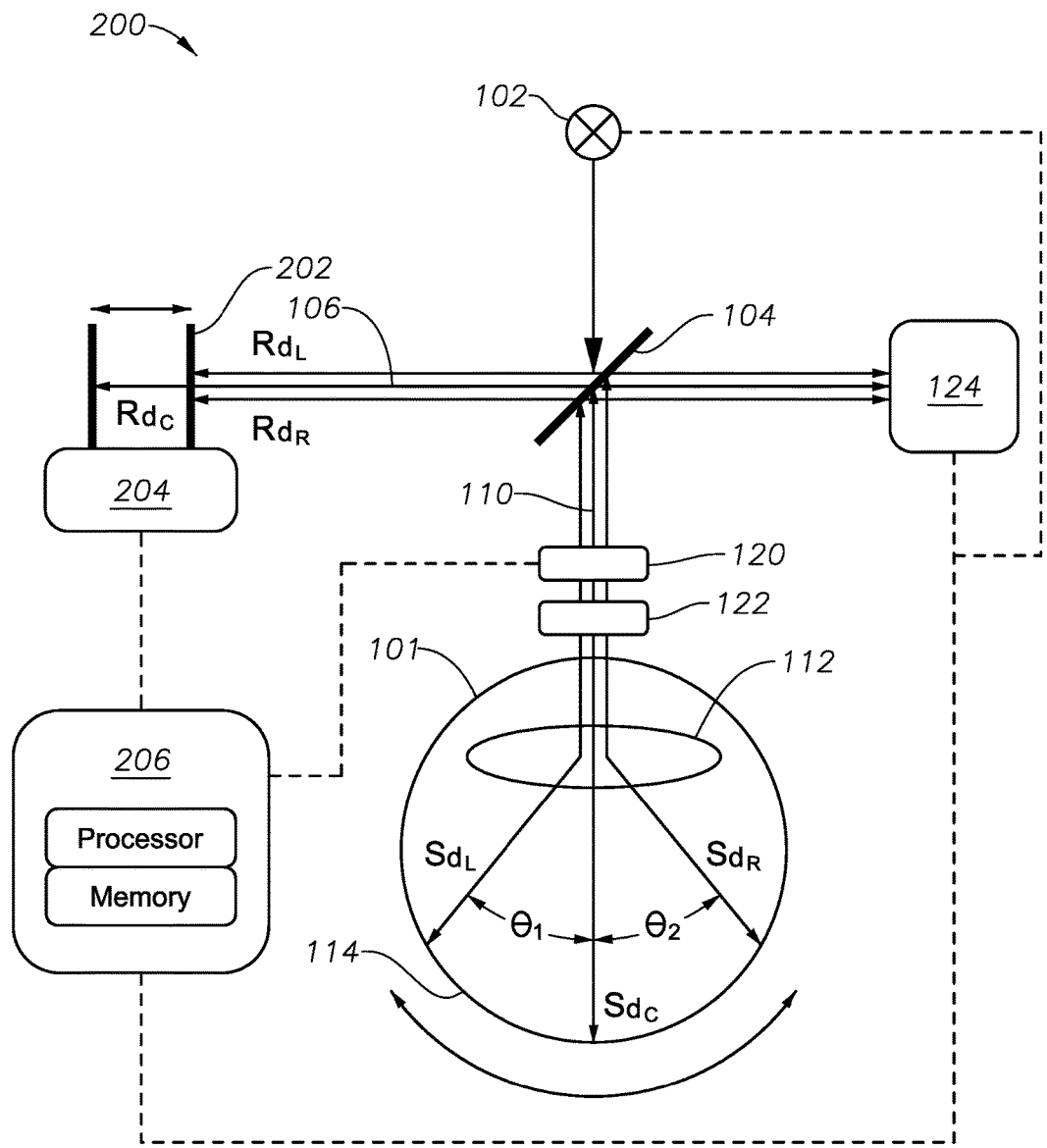
FIG. 4 illustrates a block diagram of an improved OCT imaging system according to certain embodiments.

FIG. 4 illustrates an example of an improved OCT imaging system 200 to generate images as shown in FIG. 3. System 200 may be a probe-based system, a stand-alone imaging system, or an imaging system integrated with other components, such as a surgical microscope. It is noted that FIG. 4 does not attempt to exhaustively illustrate all components of an OCT system, nor is it drawn to scale. Rather, it is provided to qualitatively illustrate how the optical path of the imaging beam 110 varies according to scan angle.

System 200 comprises an SD-OCT or SS-OCT imaging system which includes many of the same components as system 100 (like numerals indicate like components). In particular, system 200 includes a light source 102, beam splitter/combiner 104, scanner 120, and a detector 124. Light source 102 may comprise any suitable low-coherence light source such as a super-luminescent diode, ultrashort (e.g., femtosecond) pulsed laser, or supercontinuum laser, and may comprise a frequency-swept or tunable laser in certain examples, such as SS-OCT systems. Beam splitter 104 may comprise a non-polarized beam splitter for splitting the OCT beam into an imaging beam transmitted through the sample arm and a reference beam transmitted through the reference arm (sometimes referred to as a delay line) of the OCT system. Beam splitter 104 also receives and combines reflected imaging light (reflected by the sample, such as eye 114) and reference light (reflected by reference reflector 202) toward detector 124. Scanner 120 may comprise one or more galvanometer-controlled mirrors to scan the imaging beam in the x-y plane through a sample arm of the OCT system toward the sample, such as retina 114. Scanner 120 may additionally include focusing optics to scan the imaging beam in a z-direction. Scanner 120 may comprise any suitable scanner, such as a galvanometer-controlled mirror scanner. The imaging beam scanned by scanner 120 is directed through optical elements 122 which may comprise focusing and/or collimating lenses of the sample arm. Detector 124 comprises an interferometer which receives the imaging beam reflected from the target and the reference beam reflected from the reflector 202 and outputs an interference signal from which an OCT image can be generated. Particular components included in detector 124 depend on the type of OCT system and may include any suitable combination of spectrometers, photodetectors, array detectors, analog-to-digital converters (ADCs), diffraction grating(s), or other components known to those skilled in the art. Detector 124 in an SD-OCT system may include a diffraction grating, lenses, and an array detector such as a charge-coupled device (CCD). Detector 124 in an SS-OCT system may include a photodetector an analog-to-digital converter.

In contrast to system 100, system 200 includes a movable reflector 202 coupled to an actuator 204, as well as an OCT controller 206 communicatively coupled to actuator 204 and scanner 120. In certain embodiments, OCT controller 206 may also be communicatively coupled to detector 124 and light source 102. Reflector 202 typically comprises a mirror, but may comprise any reflector suitable for reflecting the reference beam of system 200 towards detector 124. In certain embodiments, actuator 204 comprises a linear actuator, such as a stacked piezoelectrionic array or linear voice coil actuator(s), configured to translate reflector 202 laterally between positions $Rd_C$ and $Rd_L/Rd_R$, as indicated by the arrow above reflector 202. In other embodiments, actuator 204 may comprise any suitable linear, rotary, or oscillatory actuator arranged to move reflector 202 and thereby adjust the reference beam path length. A stacked piezo array or voice coil actuator may provide increased simplicity compared with the galvanometer mirrors used for delay line modulation in time-domain OCT systems.

OCT controller 206 comprises hardware and software configured to perform the enhanced OCT imaging processes described herein. In certain embodiments, the OCT controller 206 includes one or more processors coupled to a memory. The processor may include one or more CPUs, microprocessors, field-programmable gate arrays (FPGAs), application-specific integrated circuits (ASICs), digital-signal processors (DSPs), system-on-chip (SoC) processors, or analogous components. The memory may include volatile or non-volatile memory including, magnetic media, optical media, random access memory (RAM), read-only memory (ROM), removable media, or analogous components. The memory may store instructions for software programs and algorithms that, when executed by the processor, allow the OCT controller 206 to direct the operation of (e.g., by generating control signals sent to) scanner 120, actuator 204, light source 102, detector 124, and/or other components of system 200 to provide improved wide-field of view OCT imaging. As used in the claims, the terms "processor," "memory," and "instructions" each refers to a classes of structures known in the field of OCT imaging and familiar to those of ordinary skill in the art. Accordingly, these terms are to be understood as denoting structural rather than functional elements of the disclosed system.

In operation, light source 102 generates an OCT beam which is split by beam splitter 104 into a reference beam 106 and an imaging beam 110. Imaging beam 110 is directed through an imaging or sample arm comprising transmission optics toward scanner 120 which, in response to signals generated by the OCT controller 206, scans the imaging beam 110 onto the target eye 101 according to a scan pattern to image a portion of the retina 114. The scan pattern executed by system 200 may be any suitable pattern, such as a raster scan, radial scan, cube scan, circle group scan, line group scan, etc.

While imaging beam 110 is scanned onto retina 114, reference beam 106 is directed toward reflector 202 through a reference arm comprising transmission optics. Actuator 204 configured to move reflector 202 in response to signals generated by the OCT controller 206 modulate the position of reflector 202 while scanner 120 scans imaging beam 110 onto retina 114 across a plurality scan angles in a scan pattern, so that the system OPD is maintained at or near zero. Detector 124 receives imaging light reflected from retina 114 and reference light reflected from the reflector 202 and outputs an interference signal from which an OCT image can be generated.

As noted above, scanner 120 may scan the target surface according to a variety of scan patterns. In certain embodiments, scanner 120 comprises two or more galvanometer scanners configured to scan imaging beam 110 according to a high-speed raster pattern. Raster patterns are typically generated using one fast galvanometer and one slow galvanometer. The fast galvanometer may sweep across a scan angle range at the raster scan frequency. In various embodiments of system 200, scanner 120 may implement a raster scan having a frequency in the range of 100-400 Hz, 150-350 Hz, 200-325 Hz, or 200-300 Hz. In certain examples, the raster scan frequency may be at least 200 Hz, 250 Hz, 275 Hz, 300 Hz, 325 Hz, 350 Hz, or 375 Hz, or 400 Hz. Further, the raster pattern may be scanned across scan angles of at least ±20 degrees (40° sweep), ±25 degrees (50° sweep), ±30 degrees (60° sweep), ±40 degrees (80° sweep), ±50 degrees (100° sweep), ±60 degrees (120° sweep), or more. The pattern may generate a B-scan at least 12 mm, 14 mm, 16 mm, 18 mm, or 20 mm, 22 mm, or 24 mm in length.

It is noted that the trajectories of imaging beam 110 and reference beam 106 depicted in FIG. 4 are simplified schematic illustrations provided to convey the principles of system 200, without concern for optical details of system 200. One skilled in the art will appreciate that, in practice, reference beam 110 and/or imaging beam 114 may be refracted and/or reflected by various elements in the beam path, including but not limited to scanner 120, optics 122, and crystalline lens 112. For example, the path of imaging beam 114 may be reflected and/or refracted between scanner 120 and lens 112, though straight paths are depicted for simplicity. Moreover, imaging beam 114

As FIG. 4 illustrates, the surface of retina 114 is curved. Thus, as imaging beam 110 is scanned across the curved surface of retina 114, the relative distance between scanner 120 (an example fixed reference point along the image beam path) and the retina 114 varies. In this example, an initial scan angle $\Theta_i=0°$ corresponds to a center-position sample distance, $Sd_C$. Although scan angles $\Theta_i$ in the example of FIG. 4 are based on a point of reference within lens 112 (where the path of imaging beam 110 at each scan angle intersects), one skilled in the art will appreciate that the location of the applicable reference point by which to measure a scan angle may vary in different embodiments.

During an imaging procedure, scanner 110 scans the imaging beam 110 so that it sweeps across retina 114, as indicated by the curved arrow below retina 114 in FIG. 4. As the scanner directs the imaging beam to the left side of retina 114, the scan angle increases from 0° to $\Theta_1$, and the distance between scanner 120 and the scanned surface of retina 114 decreases moving from $Sd_C$ to the left-position sample distance $Sd_L$ (though it is noted that the actual change in beam path length may be impacted by other features in the imaging arm of system 200). Likewise, as scanner 120 causes the beam to sweep to the right side of retina 114, the scan angle returns to 0° at $Sd_C$ and then increases to $\Theta_2$, and the distance between scanner 120 and retina 114 returns to $Sd_C$ and then increases moving to the right-position sample distance $Sd_R$ (again, the actual change in beam path length may be also impacted by other features in the imaging arm). Hence, the imaging beam path length in system 200 varies according to the scan angle of the imaging beam. Given a fixed reference beam path length, this variation can cause the OCT image to "fall off" at the edges in a "U" shape, as depicted in FIG. 2.

System 200 reduces or eliminates such distortion by adjusting the position of reflector 202 according to the scan angle to offset variations in the imaging beam path length. In particular, OCT controller 206 controls actuator 204 to modulate the position of reflector 202 synchronously with the scan angle and maintain OPD at or near zero, or within a tolerance range. For example, when scanner 120 scans imaging beam 110 to the center of retina 114, the sample beam 110 traverses a center-position path distance represented by $Sd_C$, and reflector 202 is positioned at a corresponding center-position reference beam distance $Rd_C$ which is equal or approximately equal to $Sd_C$, such that OPD is at or near zero. When scanner 120 scans imaging beam 110 at scan angle $\Theta_L$, imaging beam 110 traverses a path represented by the left sample beam distance $Sd_L$, and reflector 202 is positioned at a left reference beam distance $Rd_L$ such that the reflector 202 is translated a distance commensurate with the change in imaging beam path length (such that OPD is kept at or near zero). This may be performed at any number of points in the scan pattern. In this manner, the path length of reference beam 106 is actively adjusted during the scan to match the variation in the path length of imaging beam 110 at different scan angles in a scan pattern.

For example, if difference in the optical path length between $Sd_C$ and $Sd_L$ is 2 mm, then an actuator 204 may translate reflector 202 by a distance $Rd_C-Rd_L$ to reduce the reference beam path length by an amount such that the OPD between reference and sample arms is kept at or near zero. It is noted that, in practice, it may be necessary to translate reflector 202 more or less than 2 mm to maintain overall OPD at or near zero. This may be at least partially caused by differences between the optical paths of the imaging beam 110 and reference beam 106. For example, the sample arm of system 200 includes scanner 120, optics 122, and eye 101. Within eye 101, the refractive index is approximately n=1.3. On the other hand, the reference beam 202 traversing the reference arm may be in air, where n=1.0. In such a system, to maintain overall OPD near zero given a 2 mm change in imaging beam path length, it may be necessary to move reference reflector 202 more than 2 mm. Accordingly, in various embodiments, specific translation distances for reference reflector 202 may be calibrated to account for system- and implementation-specific factors to maintain OPD at or near zero or within a tolerance range.

In some examples, system 200 may maintain equal imaging beam and reference beam path lengths (OPD=0) for all scan angles $\Theta_n$ in a scan pattern. However, in other examples, it may not be necessary or feasible to maintain OPD at exactly zero for all scan angles. Accordingly, in certain embodiments OPD may be maintained within a tolerance value $Td_X$, such that any difference between the imaging beam path length and reference beam path length is less than or equal to $Td_X$ (e.g., $|OPD| \leq Td_X$ for all scan angles $\Theta_n$ in a scan pattern). In some examples, $Td_X$ may be 0.1 mm, 0.25 mm, 0.5 mm, 1 mm, or any other suitable value. In certain examples, $Td_X$ may be variable. For example, $Td_X$ may increase or decrease depending on the scan angle. $Td_X$ may be set or configured by a system operator.

In the context of a retinal imaging procedure, a raster pattern executed across wide angles at high rates presents particular challenges because the imaging beam path length changes most rapidly as retina 114 is scanned in a straight line. Hence, a high-frequency raster pattern requires that the reference beam path length must be modulated at a very high speed. To modulate the reference beam path length synchronously with the fast galvanometer executing a high-speed, wide-angle raster scan, actuator 204 may include one or more linear actuators 204 configured to move reflector 202 (under the control of OCT controller 206) synchronously with the movement of scanner 120. For example, linear actuators 204 comprise stacked array of piezoelectric actuators having at least 2 mm of stroke, operated in a double-path delay line to yield over 4 mm of effective reference beam path length modulation (e.g., by moving reflector 202 across a 4+mm range between $Rd_C$ and $Rd_L/Rd_R$). In other examples, actuators 204 may comprise linear voice coil actuator(s) configured to modulate the position of reference reflector 202 across a a 4+mm range between $Rd_C$ and $Rd_L/Rd_R$.

Values defining the correct position of reference reflector 202 at particular scan points and/or scan angles in a scan pattern may comprise pre-loaded default values. Alternatively, such values may be input by a system operator or generated from patient-specific data. Such patient-specific data may comprise eye modeling data, biometric data, OCT image data, and/or any other suitable information, including data obtained during a preoperative procedure or during a calibration or initialization phase of an imaging procedure.

For example, in certain embodiments, OCT controller 206 may cause scanner 120 to generate a calibration OCT image by scanning the imaging beam 110 according to a scan pattern while reflector 202 remains stationary in an initial position. OCT controller 206 may receive and analyze the generated calibration OCT image to determine a plurality of sample distance values (e.g., $Sd_1, Sd_2, \ldots Sd_n$) associated with particular scan angle values (e.g., $\Theta_1, \Theta_2, \ldots \Theta_n$). Based on the sample distance values, OCT controller 206 may calculate a plurality of reflector position values (e.g., $Rp_1, Rp_2, \ldots Rp_n$) which will change the reference beam path length to maintain the OPD within the specified tolerance. OCT controller 206 may then associate the calculated reflector position values with corresponding scan angle values and store the association in memory. During an imaging procedure, OCT controller 206 may generate signals which cause scanner 120 to scan imaging beam 110 across scan angles in the scan pattern and simultaneously control actuator 204 to position of reflector 202 according to the stored reflector position values associated with each scan angle. As a result, reflector 202 may sweep across a plurality of positions synchronously with the scan rate, thereby adjusting the length of the reference beam to maintain OPD within a desired tolerance $Td_X$.

Accordingly, embodiments of system 200 are capable of providing an ultra-wide field-of-view OCT image of a target, such as a retina, at high scan rates without image distortion characteristic of conventional OCT systems. Although a curved target surface is discussed in the example of FIG. 4, the systems and advantages described in the present disclosure may not be confined to imaging curved target surfaces but also include enhanced imaging of flat target surfaces based on the same principles.

Figure 5:
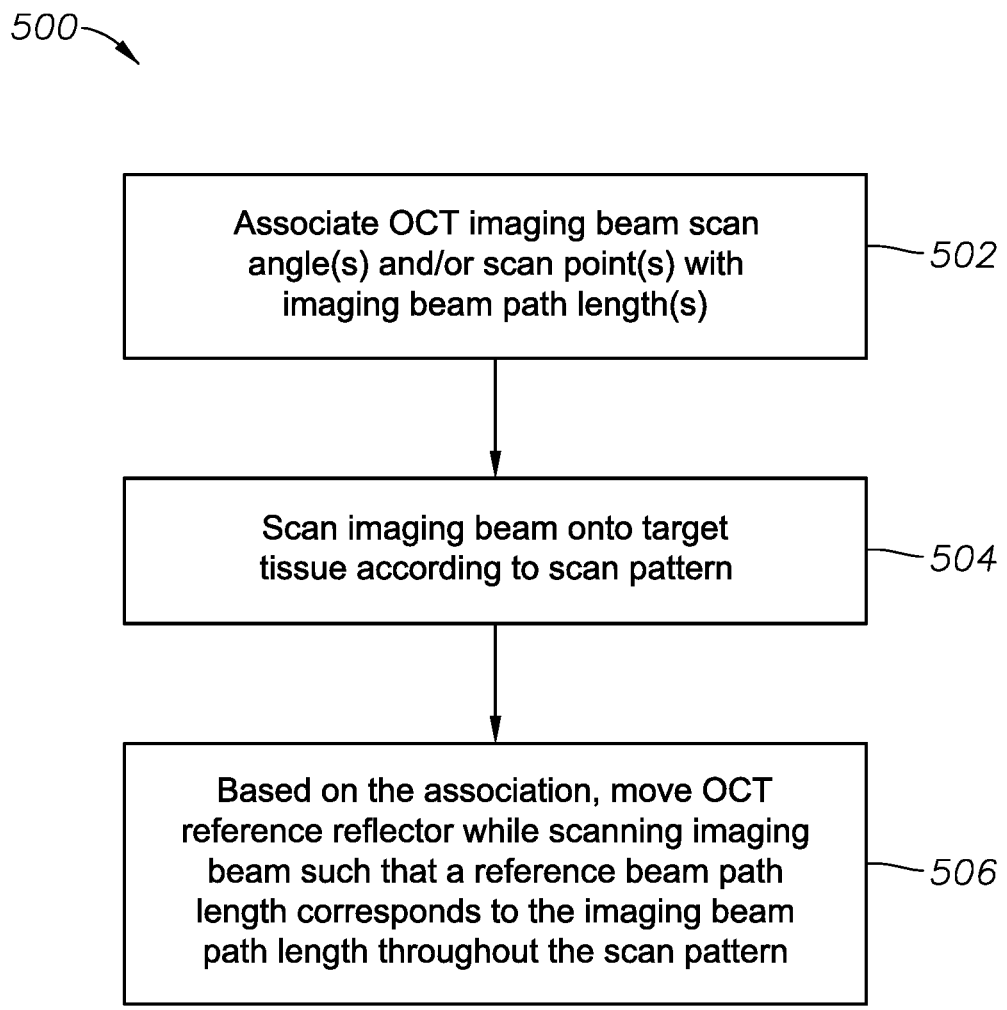
FIG. 5 illustrates a method performed by an improved OCT imaging system according to certain embodiments.

FIG. 5 depicts a process performed by components of system 200 in certain embodiments. At step 502, an OCT controller 206 of system 200 associates one or more scan angles of a scan pattern with a plurality of reference reflector positions. The associations may be pre-loaded or calculated based on input by a system operator. In certain embodiments, the associations are determined by an OCT controller 206 based on patient data, eye modeling data, OCT image data, and/or other information. In certain embodiments, an OCT controller 206 calculates and stores a reference reflector position value for each of a plurality of scan angles in a scan pattern based on an analysis of a calibration OCT image. The calculated reflector position values for each scan angle may, in certain embodiments, also account for characteristics or features in the imaging beam path, such as the refractive index of eye 101. In some embodiments, the pattern may be scanned across scan angles of at least ±20 degrees (40° sweep), ±25 degrees (50° sweep), ±30 degrees (60° sweep), ±40 degrees (80° sweep), ±50 degrees (100° sweep), ±60 degrees (120° sweep), or more. The pattern may be a raster pattern generating a B-scan at least 12 mm, 14 mm, 16 mm, 18 mm, 20 mm, 22 mm, or 24 mm in length. The scan pattern may be selected by a user or automatically selected by system 200.

At step 504, an OCT controller 206 generates signals to cause scanner 120 to scan imaging beam 110 onto retina 114 at each scan angle within the scan pattern. In certain examples, the scan frequency may be at least 200 Hz, 250 Hz, 300 Hz, 325 Hz, 350 Hz, or 375 Hz, or 400 Hz.

At step 506, based on the association at step 502, the OCT controller 206 generates signals causing the actuator 204 (e.g., a stacked piezo array or voice coil actuator(s)) to move reference reflector 202 while imaging beam 110 is scanned at step 504 such that the reference beam path length is modulated according to the imaging beam path length throughout the scan pattern, so that the $|OPD| \leq Td_X$ for all or a subset of scan angles $\Theta_n$ in the scan pattern. In other embodiments, the OCT controller may generate an instruction set which combines a reflector position sequence with the scan pattern. The instruction set may be executed by a processor of the OCT controller 206 without interruptions or delays attributable to on-the-fly calculations or lookup operations.

In this manner, an improved OCT image may be generated that "flattens out" the characteristic "U" shape, as shown in FIG. 3. This allows for imaging and analysis of a greater portion of the retinal surface may be imaged and, in contrast to FIG. 2, a surgeon may easily "zoom in" to any of windows A, B, or C of FIG. 3 to view a particular area of the retina in greater detail. Compared with FIG. 2, the OCT image shown in FIG. 3 is more easily readable and more useful to surgeons, particularly for intraoperative real-time imaging.

Accordingly, embodiments of the disclosure provide methods and systems for wide field-of-view OCT imaging which overcomes limitations of conventional systems and methods. It will be appreciated that above-disclosed and other features and functions, or alternatives thereof, may be desirably combined into many other different systems or applications in accordance with the disclosure. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. An optical coherence tomography (OCT) system, comprising:
   a light source, configured to generate an OCT beam;
   a beam splitter, configured to:
      split the OCT beam into a reference beam and an imaging beam;
      direct the reference beam toward a reference reflector; and
      direct the imaging beam toward a scanner;
   a linear actuator, configured to move the reference reflector to adjust the length of the reference beam;
   the scanner, configured to scan the imaging beam onto a target surface at a plurality of scan angles, wherein the scanner and target surface are separated by a sample distance that varies at each of the scan angles;
   an OCT controller comprising a processor and instructions stored on a memory, the instructions executable by the processor to cause the OCT controller to generate signals to:
      cause the scanner to scan the imaging beam at each of the scan angles at a first scan rate; and
      cause the actuator to adjust the length of the reference beam during the scan synchronously with the scan rate to offset the variation in sample distance at each of the scan angles.

2. The system of claim 1, wherein the scan rate is between 200 Hz and 400 Hz.

3. The system of claim 1, wherein the scan rate is at least 300 Hz.

4. The system of claim 1, wherein the scanner is configured to scan the imaging beam at each of the scan angles according to a raster pattern.

5. The system of claim 4, wherein the raster pattern generates a B-scan at least 12 mm in length.

6. The system of claim 4, wherein the raster pattern generates a B-scan at least 16 mm in length.

7. The system of claim 1, wherein the linear actuator comprises a piezoelectric actuator or voice coil actuator, configured to translate the reference reflector at least 2 mm in a direction parallel to the reference beam.

8. The system of claim 1, wherein the linear actuator comprises a piezoelectric actuator or voice coil actuator, configured to translate the reference reflector at least 4 mm in a direction parallel to the reference beam.

9. The system of claim 1, wherein the OCT system comprises a spectral-domain OCT (SD-OCT) system or a swept-source OCT (SS-OCT) system.

10. An optical coherence tomography (OCT) system, comprising:
   a light source, configured to generate an OCT beam;
   a beam splitter, configured to:

split the OCT beam into a reference beam and an imaging beam;
direct the reference beam toward a reference reflector; and
direct the imaging beam toward a scanner;
a linear actuator, configured to move the reference reflector to change the length of the reference beam; and
the scanner, configured to scan the imaging beam onto a target surface over a plurality of scan angles, wherein the scanner and target surface are separated by a first sample distance at a first scan angle and a second sample distance at a second scan angle;
an OCT controller comprising a processor and instructions stored on a memory, the instructions executable by the processor to cause the OCT controller to generate signals to:
cause the scanner to scan the imaging beam onto the target surface at the first scan angle and the second scan angle according to a scan rate; and
cause the actuator to move the reference reflector synchronously with the scan rate while the scanner scans the imaging beam onto the target surface, thereby adjusting the length of the reference beam to account for a difference between the first sample distance and the second sample distance; and
a detector configured to:
receive the reference beam reflected by the reference reflector and the imaging beam reflected by the target surface; and
output an interference signal based on the received reference beam and the imaging beam.

11. The system of claim 10, wherein the linear actuator comprises a piezoelectric stack or a voice coil actuator, configured to translate the reference reflector at least 2 mm in a direction parallel to the reference beam.

12. The system of claim 10, wherein the first scan angle and the second scan angle are separated by at least 20 degrees.

13. The system of claim 10, wherein the scan generates a B-scan at least 12 mm in length.

14. The OCT system of claim 10, wherein the OCT system comprises a spectral-domain OCT (SD-OCT) system or a swept-source OCT (SS-OCT) system.

15. An optical coherence tomography (OCT) system, comprising:
a light source, configured to generate an OCT beam;
a beam splitter, configured to:
split the OCT beam into a reference beam and an imaging beam;
direct the reference beam toward a reference reflector; and
direct the imaging beam toward a scanner;
a linear actuator, configured to translate the reference reflector at least 2 mm in a direction parallel to the reference beam;
the scanner, configured to scan the imaging beam onto a target surface at a plurality of scan angles;
an OCT controller comprising a processor and instructions stored on a memory, the instructions executable by the processor to cause the OCT controller to generate signals to:
cause the scanner to scan the imaging beam at each of the scan angles at a first scan rate; and
move the actuator to translate the reference reflector synchronously with the scan rate, such that a path length of the reference beam is maintained within a tolerance range of a path length of the imaging beam throughout the scan.

16. The OCT system of claim 15, wherein the tolerance range is less than 1 mm.

17. The system of claim 16, wherein the scan rate is between 200 Hz and 400 Hz.

18. The system of claim 15, wherein the scanner is configured to scan the imaging beam at each of the scan angles according to a raster pattern.

19. The system of claim 15, wherein the linear actuator comprises a piezoelectric actuator or a voice coil actuator, configured to translate the reference reflector at least 2 mm in a direction parallel to the reference beam.

* * * * *